United States Patent [19]

Horiba et al.

[11] 4,257,102
[45] Mar. 17, 1981

[54] APPARATUS FOR AXIAL TRANSVERSE TOMOGRAPHY

[75] Inventors: Isao Horiba, Nagoya; Yasuo Kuwabara, Kashiwa; Hiroshi Takagi, Tokyo; Shigeru Satou, Matsudo, all of Japan

[73] Assignee: Hitachi Medical Corporation, Tokyo, Japan

[21] Appl. No.: 953,773

[22] Filed: Oct. 19, 1978

[30] Foreign Application Priority Data

Oct. 19, 1977 [JP] Japan ................. 52-124570

[51] Int. Cl.² .......................................... G01N 23/00
[52] U.S. Cl. ................................. 364/414; 250/445 T
[58] Field of Search ........................ 364/414, 415; 250/445 T, 445 R, 369

[56] References Cited

U.S. PATENT DOCUMENTS

| | | | |
|---|---|---|---|
| 4,032,761 | 6/1977 | Mayo et al. | 364/414 |
| 4,063,074 | 12/1977 | Wagner | 364/414 |
| 4,070,707 | 1/1978 | Barber | 364/414 |
| 4,117,336 | 9/1978 | Bates | 364/414 X |
| 4,136,388 | 1/1979 | Lindquist | 364/414 |

Primary Examiner—Edward J. Wise
Attorney, Agent, or Firm—Gerald J. Ferguson, Jr.; Joseph J. Baker

[57] ABSTRACT

An apparatus for axial transverse tomography using piercing radiation such as X-ray and γ-ray for displaying a tomographic image concerning variation of radiation absorption values at a given section of a subject under examination, comprising: a scanner effecting a revolution-scanning around said subject at uniform angles while maintaining constant relative positions of a radiation source and a radiation detector with said subject intervening therebetween; an input device for setting a region of interest for being enlarged based on parameters of central angle, inter-center distance and radius ratio, to locally enlarge said tomographic image; co-ordinate system transforming circuitry for carrying out, on information within said region of interest outputted from radiation detector, a transformation of co-ordinate system corresponding to enlarged co-ordinates, from information obtained by the scanner and outputted by the radiation detector and also from the set parameters; and convolution circuitry for carrying out a convolution operation on the resulting information representing the transformation of co-ordinate system.

6 Claims, 8 Drawing Figures

APPARATUS FOR AXIAL TRANSVERSE TOMOGRAPHY

BACKGROUND OF THE INVENTION (a) Field of the Invention

The present invention concerns an apparatus for axial transverse tomography for displaying a tomographic image obtained on the basis of variation of X-ray absorption at an imaginary flat slice portion in a subject under examination, by the use of piercing radiation such as X-ray or γ-ray. More particularly, the present invention relates to an apparatus for axial transverse tomography equipped with a function for enlarging a tomographic image.

(b) Description of the Prior Art

In the past, as means for enlarging a tomographic image, there have been proposed methods such as a method utilizing scan converter and a method for continuously enlarging a digitalized image through interpolation by the use of a memory device. Each of these conventional methods, however, is such that the spatial resolving power of image becomes degraded as the magnifying power increases.

SUMMARY OF THE INVENTION

It is an object of the present invention to provide an apparatus for axial transverse tomography which is capable of improving degradation of spatial resolving power of image due to magnification, and which is capable of making an efficient image re-construction and of providing a good tomographic image by omitting the mathematical operation not required, thereby eliminating the inconvenience of the conventional methods.

For achievement of the object, apparatus for axial transverse tomography according to the present invention comprises: scanning means for effecting scanning while revolving around a subject under examination and while maintaining constant the relative positions of radiation source and a radiation detector which are disposed to sandwich said subject under examination therebetween; setting means for setting a region of interest for being enlarged, by the use of parameters represented by a central angle, an inter-center distance and a ratio of radii, for locally enlarging a tomographic image; co-ordinate system transforming means for effecting transformation of co-ordinate system, corresponding to enlarged co-ordinates, for the output information of the radiation detector concerning the region of interest from the general output information of the radiation detector which is obtained by said scanning and also from said set parameters; and mathematical operating means for making convolution operation only for that portion which is necessary for re-construction of enlarged image based on the information representing transformed coordinate system.

In the present invention, convolution operation (multiple integral) is employed as a general means for seeking a tomographic image concerning variation of the radiation absorption values of the subject under examination, by processing a ground of information obtained by irradiation of radiation, in various directions, at a imaginary slice surface of the subject under examination by the use of piercing radiation. The present invention contemplates effecting transformation of co-ordinate system of information corresponding to the co-ordinates of the enlarged image portion from the group of informations obtained by revolution-scanning, and effecting a precision enlargement of the image through local convolution operation.

DETAILED DESCRIPTION OF THE PREFERRED EMBODIMENTS

Figure 1:
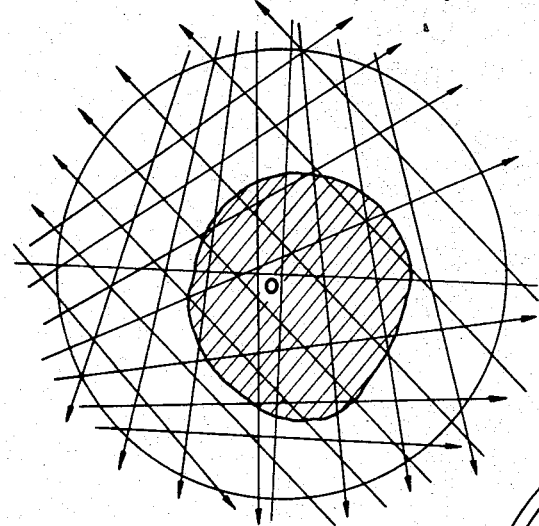
FIGS. 1 through 3 are explanatory illustrations of transformation of co-ordinate system for local enlargement of image in the present invention.
Figure 2:
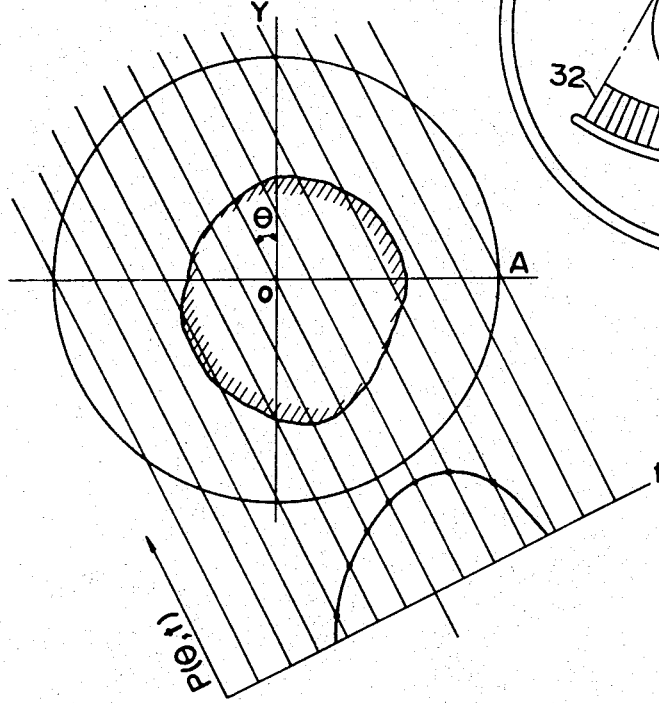
Figure 3:
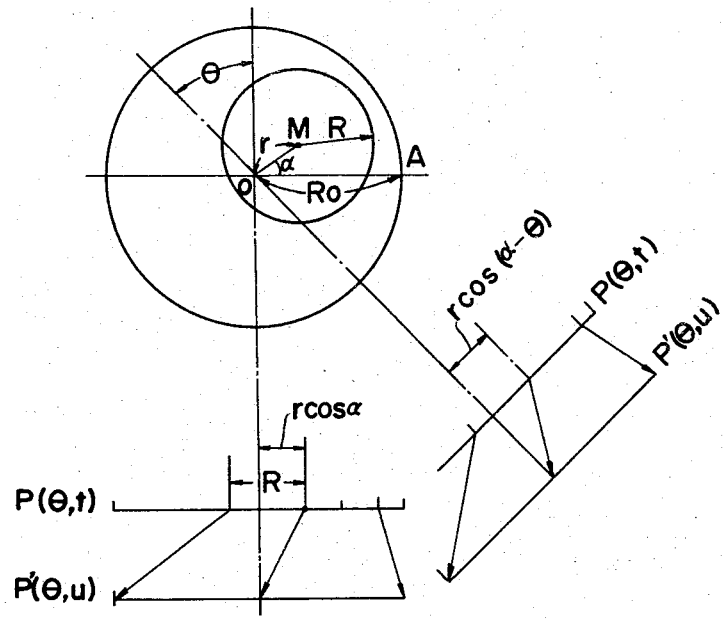

Description will hereunder be made of transformation of coordinate system effected for local enlargement of image in the apparatus according to the present invention, by referring to FIGS. 1 through 3.

With respect to a region defined by a radius $OA = R_o$, radiation beams are irradiated in the directions of arrows as shown in FIG. 1, and those beams of radiation are measured in mesh form in various directions, and the resulting group of informations outputted from the radiation detector is subjected to appropriate interpolation and re-arrangement into a group of informations wherein the angle θ (which, in the example of FIG. 2, represents the angle of inclination of beam of radiation relative to axis OY among the spatial coordinates) is constant and the relation of position t varies. Here, the angle of the re-arranged group of information will be expressed as θ relative to the original point O of the real space, and the positional co-ordinate will be expressed as t, and the value of measurement will be expressed as P (θ, t). The manner for constructing an enlarged information P' (θ, u) from said group of informations P (θ, t) is shown in FIG. 3. In FIG. 3, the larger circle of radius $R_o$ represents the region allowing the measurement of information to be made. The smaller circle of radius R represents the region of interest for being enlarged, i.e. the specific part of the image for being enlarged. In such an instance, this region of interest is such that its position within the information-measurment-possible region and its size are determined by designating the three parameters which are: central angle α, inter-center distance r and radius ratio $R_o/R$. M represents the central point of the region of interest. The apparatus of the present invention is intended to enlarge the portion defined by radius R about point M into a circle defined by radius $R_o$ about point O.

From FIG. 3, it will be understood that between the measurement value P (θ, t) and the enlarged information P' (θ, u), there is the following relationship:

$$u = R_o/R \{t - r \cos(\alpha - \theta)\} \ldots \quad (1).$$

Accordingly, by subjecting the measured P (θ, t) to the transformation of the above-mentioned Equation (1) and to a convolution operation, and by adding the result to the right-angle co-ordinates, the region of interest of radius R about point M can be expressed in an enlarged fashion as a region of radius $R_o$ about point O.

In Equation (1), since $R_o > R$, it should be understood that when the sampled measurement information is handled, the sampling pitch of the positional function t is enlarged by said transformation, and it will become possible to obtain an image quality same as that noted prior to the enlargement, by performing the measurement with a pre-arranged pitch representing multiplication by $R/R_o$ time corresponding to a magnification.

Figure 4:
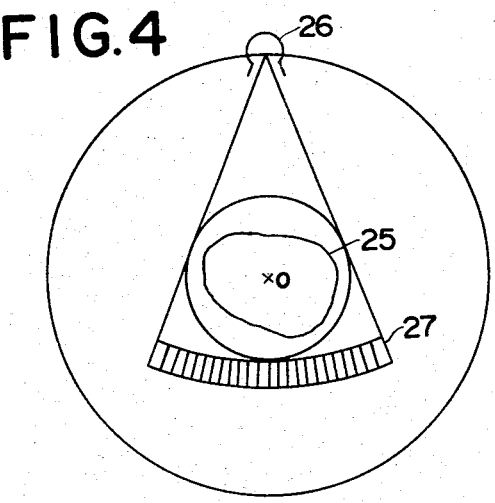
FIG. 4 is a diagrammatic representation of an example of the information-taking part employed in the present invention.
Figure 5:
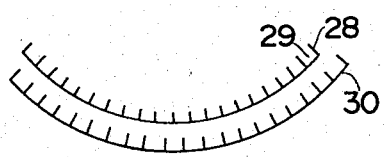
FIG. 5 is an explanatory illustration of movement of the radiation detector at the time of making precision mesurement in the present invention.

FIG. 4 shows the information measurement portion in the apparatus of the present invention, and it is the body-axis transversing apparatus using X-ray as the source of piercing radiation. The measurement employs diverging fan-like beams. The measurement is carried out by the use of an X-ray generator 26 and an X-ray detector (not shown) which is formed by, for example, 256 detecting elements 27 for detecting the X-ray having passed through the body of the subject 25 under examination, and by causing these two members 26 and 27 to revolve about point O while maintaining their relative positions constant, while sandwiching the subject under examination between them. Measurement is performed once for every one degree of angle during the revolution through 360 degrees, so that there are carried out 360 measurements in total throughout one whole revolution. In case it is intended to obtain an image of a higher precision, the detector is displaced in position from position 28 over to position 30 as shown in FIG. 5. More specifically, the relative positions of the X-ray generator and the X-ray detector are displaced through one half of the size of a single detecting element, and then a whole revolution is covered to make 360 measurements. As a result of this latter scanning, there can be obtained, at the time of a precision measurement, $256 \times 360 \times 2 = 184,320$ pieces of information as contrasted to $256 \times 360 = 92,160$ pieces of information at normal measurement.

Figure 6:
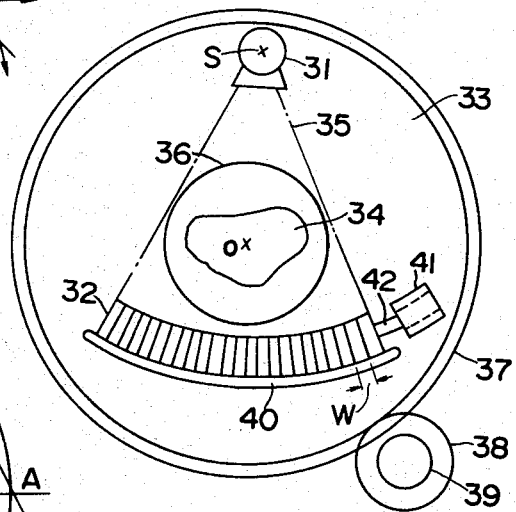
FIG. 6 is a diagrammatic representation of an example of the revolution-scanning means employed in the present invention.

The scanning means for effecting revolution-scanning about the subject under examination while maintaining constant the relative positions of the radiation source and the radiation detector which are arranged with the subject lying between them is shown in FIG. 6. This represents the instance wherein X-ray is used as the radiation, and wherein the information of axial transversion of a subject under examination is sought on the basis of X-ray having passed through the body of the subject. In FIG. 6, 31 represents an X-ray generating source. 32 represents an X-ray detector comprising a number of elements of, for example, 256 in number. 33 represents a frame which, in this instant example, is comprised of a disk-like frame. The X-ray generating source 31 and the X-ray detector 32 are mounted on this disk-like frame 33. 34 represents a subject under examination. 35 represents diverging fan-like beams of X-ray emitting from the X-ray generating source 31. 36 represents an opening for scanning which is formed to pass through the central portion of the disk-like frame 33. 37 represents circumferential teeth secured to the outer periphery of the frame 33. 38 represents a toothed wheel engaging the circumferential teeth 37 of the frame 33. 39 represents a motor for driving the toothed wheel 38. 40 represents a guide rail for guiding the displacement of the X-ray detector 32. 41 represents a driving solenoid for use as a driving source of the displacement of the X-ray detector 32. 42 represents a driving shaft which is driven by the driving solenoid 41.

The scanning mechanism functions as stated below. The X-ray generating source 31 emits a fan-shaped diverging X-ray beam from its focus S to be irradiated onto the subject 34 under examination. The X-ray detector 32 detects the fan-shaped X-ray beam which has passed through the subject 34 under examination, and collects the information of that portion of the subject 34 through which the X-ray beam has passed. Furthermore, this collection of information includes respective information on irradiations of X-ray beam irradiating in other directions of the subject 34. Such collection of various informations is achieved by causing a revolution of the frame 33 on which the X-ray generating source 31 and the X-ray detector 32 are mounted. More particularly, on the frame 33 are secured circumferential teeth, and these circumferential teeth 37 are in engagement with the toothed wheel 38, so that the revolution force of the motor 39 is transmitted to the frame 33 via the toothed wheel 38. Thus, the frame 33 is caused to rotate about the central point O of the scanning area.

Furthermore, at the time of measurement of a higher precision, the relative relationship in which the X-ray generating source 31 faces the X-ray detector 32 is displaced by a distance representing one half of the size of the detecting element which constitutes the X-ray detector 32. The arrangement intended to make this displacement comprises the guide rail 40, the driving solenoid 41 and the driving shaft 42. An end of the driving shaft 42 is fixed to an end of the X-ray detector 32, and the other end of this driving shaft 42 is inserted into the coil of the driving solenoid 41. Arrangement is provided so that the position of the driving shaft 42 will be displaced through one half of a distance which is the size of any one detecting element of the X-ray detector 32 between the following two kinds of state, i.e. when the driving solenoid 41 is rendered to its energized state and when this solenoid 41 is rendered to its de-energized state. As a result, the X-ray detector 32 is caused to turn, while being guided by the guide rail 40 through a distance corresponding to one half of the size of a single detecting element, about the focus S of the X-ray generating source 31.

Figure 7:
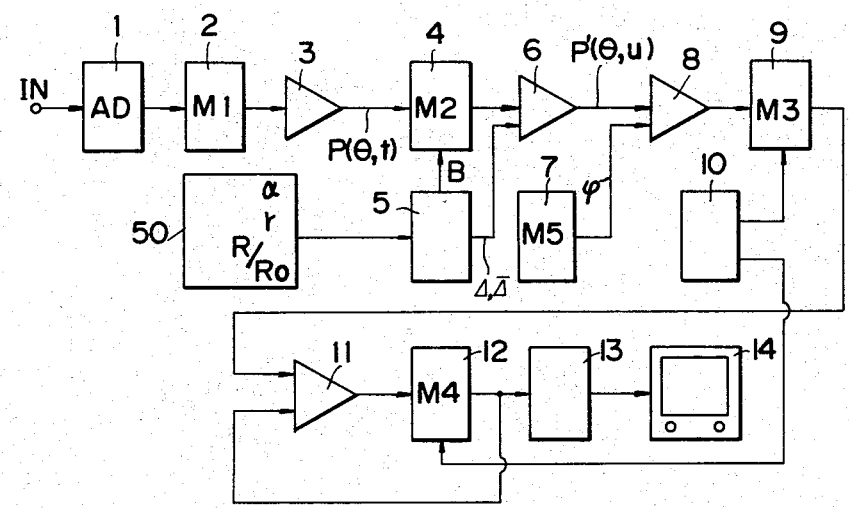
FIGS. 7 and 8 are block diagrams of an example of information-processing in the present invention.
Figure 8:
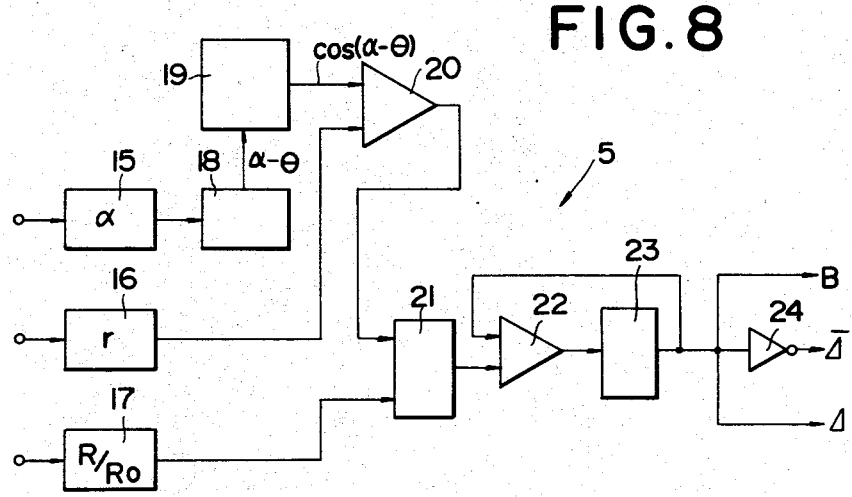

FIGS. 7 and 8 are block diagrams of an example of information processing according to the present invention. The information which has been measured by the detector by the use of the apparatus shown in FIG. 6 is passed through a logarithm converter not shown to be converted to an amount representing the accumulated value of the X-ray absorption values in the path of the X-ray beam, and the result is inputted to the input terminal IN shown in FIG. 7. This input signal is converted by an AD converter 1 to a digital amount and is entered in a buffer memory 2 (which is indicated by M1 in the block diagrams). 3 represents a computing element for re-arrangement. This re-arranging computing element transforms the information which has been measured by the use of the fan-like X-ray beam to the information P ($\theta$, t) which has been described in connection with FIG. 2. This information P ($\theta$, t) ranges from 0 to 1, 2, 3, ..., 359 with respect to angle variable $\theta$, and normally 256 with respect to position variable t, and at the time of a precision measurement, it covers information of 512 with respect to position variable. The information is entered in a buffer memory. 6 represents a computing element intended for enlargement, and is comprised of an interpolating a computing element. 5 represents a control means for controlling this enlargement operation. This control means carries out the operation of Equation (1) based on the three parameters, i.e. central angle $\theta$, intercenter distance r and radius ratio $R_o/R$, which are designated on the input side and which define that specific portion for being enlarged, i.e. the aforementioned region of interest for being enlarged, and thus it gives out the enlarged information $P'(\theta, u)$.

FIG. 8 shows the details of the control means 5 illustrated in FIG. 7. The parameters $\alpha$, $R/R_o$ and r are entered in registers 15, 16 and 17 by an inputting means 50, respectively, and the parameters $R/R_o$ can be formed by, for example, a device based on a synthesizing method of Lissajous' Figure using two oscillators. 18 represents a presettable counter which functions so as to first pre-set the inter-center angle signal $\alpha$ from the register 15, and thereafter to make a deduction of the number of counts by one count for each advancement of the revolution angle $\theta$ covered by both the radiation source and the radiation detector. The memory 19 contains therein tabulated cosine functions. The output of the presettable counter 18 is inputted to the address line of the memory 19, and this memory 19 generates the cosine value $\cos(\alpha-\theta)$ of the content of the count entered in the presettable counter 18. This output signal is multiplied in a multiplier 20 with the inter-center distance signal delivered from the register 16, and the result is entered in a register 23 through a multiplexer 21 and an adder 22. This value is read out from the register 23. The adder 22 adds up this read-out value to the radius ratio signal $R/R_o$ which is read out from the register 17, and outputs a signal $R/R_o + r \cdot \cos(\alpha-\theta)$. The register 23 carries out write-in and read-out simultaneously in accordance with the inputting of a clock pulse thereto. Whereby, the addition of the radius ratio signal $R/R_o$ is repeated in succession for u times, and thus $t = \{R/R_o \cdot u + r \cdot \cos(\alpha-\theta)\}$ is outputted. Let us now assume that the integer part of this $t = \{R/R_o \cdot u + r \cdot \cos(\alpha-\theta)\}$ is represented by B and the decimal part thereof is represented by $\Delta$. Then, t is of the relationship: $t = B + \Delta$. The signal B of the integer part is inputted into the address line of the buffer memory 4, and it reads out an information $P(\theta, B)$ and an information $P(\theta, B+1)$, and inputs these informations into computing element 6, which carries out an operation of $P'(\theta, u) = \overline{\Delta} \times P(\theta, B) + \Delta \times P(\theta, B+1)$ from the above-mentioned two kinds of informations and also from the decimal part signal $\Delta$ and from an inverted decimal part signal $\overline{\Delta}$ which is generated by a code inverting circuit 24.

Returning now to FIG. 7, reference numeral 8 represents a convolution computing element which carries out convolution processing of the enlarged information $P'(\theta, u)$ which is outputted from computing element 6 for enlargement by the use of a weight function $\phi$ which is read out from a memory 7 which contains a weight function table, and the result of this processing is entered into a buffer memory 9. 12 represents an image re-construction memory which functions so that the information which has been entered in the buffer memory 9 is taken-in via computing element 11, and a cumulative addtion processing is carried out therein. 10 represents a control means for this cumulative addition processing, and it controls the address line of the buffer memory 9 and of the image re-construction memory 12. The re-constructed image is transformed by a TV signal converter 13 into a video signal, and is expressed at an image display device 14.

According to the apparatus shown in FIGS. 6 through 8, an enlargement of any arbitrary portion of image can be made up to two (2) magnifications at the time of a precision measurement, without degrading the quality of the image. Also, the convolution operation can be achieved always by a certain minimum number of convolution operations without depending on the magnifying rate. It should be understood here that, in the above-mentioned example, description has been made of the instance wherein the X-ray detector is displaced at the time of precision measurement. It is needless to say that, instead of displacing the detector, the X-ray generating source may be displaced in such precision measurement.

According to the apparatus of the present invention, it is possible to improve degradation of the spatial resolving power of image accruing from enlargement of image, and also it is possible to omit the processing of portions which are not enlarged. Thus, the operation becomes a very efficient one, and the length of time required for the processing can be reduced significantly.

What is claimed is:

1. An apparatus for axial transverse tomography using piercing radiation such as X-ray and $\gamma$-ray for displaying a tomographic image concerning variation of radiation absorption values at a given section of a subject under examination, comprising:

scanning means effecting a revolution-scanning around said subject at uniform angular increments while maintaining constant relative positions of a radiation source and a radiation detector with said subject intervening therebetween;

setting means for defining a region of interest to be enlarged defined by parameters of central angle $\alpha$, intercenter distance r and radius ratio $R_o/R$ where $R_o$ is the radius of the region scanned by said scanning means, R is the radius of said region of interest to be enlarged, the latter region being with the scanned region of radius $R_o$ so that $R_o > R$, r is the distance between (a) the center of the scanned region and (b) the center of the region of interest to be enlarged and (c) $\alpha$ is the angle between the aforementioned centers in a predetermined co-ordinate system where the center of the scanned region is located at the center of the said co-ordinate system to locally enlarge said tomographic image;

co-ordinate system transforming means responsive to said scanning means and said setting means for transforming the co-ordinates of said absorption values within said region of interest to co-ordinates in an enlarged region corresponding to the scanned region; and means for carrying out a convolution operation on the absorption values resulting from said co-ordinate system transformation means so that the convolution operation is performed only on absorption values within said region of interest to thereby effect the enlargement of the region to be enlarged with minimal degradation of the enlarged image resolution.

2. An apparatus according to claim 1, in which: said scanning means firstly revolves around said subject at uniform angles, and thereafter carries out similar revolution-scanning after displacement of the relative positions of said radiation source and said radiation detector through an amount corresponding to one half of a size of any single detecting element constituting said detector.

3. Apparatus as in claim 1 where the revolution-scanning about said subject is with respect to the angle $\theta$ so that for each said angular increment, a new value of $\theta$ occurs and where said scanning means includes means for obtaining a plurality of laterally displaced measurements of said absorption values for each said new value of $\theta$ where said laterally displaced measurements are with respect to the variable t, said apparatus further including means for obtaining for each value of said absorption values as a function of $\theta$ and t, that is, $P(\theta,t)$.

4. Apparatus as in claim 3 where the absorption values corresponding to said scanned region are $P(\theta,t)$ and where said region of interest to be enlarged corresponds to a predetermined portion of the $P(\theta,t)$ absorption values.

5. Apparatus as in claim 4 where said co-ordinate system transforming means transforms the co-ordinate of the absorption values $P(\theta,t)$ to co-ordinates of absorption values $P'(\theta,\mu)$ in said enlarged region where for each said value of $\theta$, $$\mu = R_o/R \{t - r \cos(\alpha - \theta)\}.$$

6. Apparatus as in claim 5 where said co-ordinate transforming means includes (a) means for obtaining $t = B + \Delta$ where $B = R/R_o \cdot \mu$ and $\Delta = r \cdot \cos(\alpha - \theta)$ and (b) means for obtaining $P'(\theta,\mu) = \overline{\Delta} \times P(\theta,B) + \Delta \times P(\theta,B+1)$ whereby $P'(\theta,\mu)$ is applied to said means for carrying out the convolution operation.

* * * * *